United States Patent
Dörhöfer et al.

[11] 3,988,467
[45] Oct. 26, 1976

[54] AMINOACYL COMPOUNDS

[75] Inventors: Günther Dörhöfer, Allschwil; Roland Heckendorn, Arlesheim; Erich Schmid, Basel; Angelo Storni, Rheinfelden; Armin Züst, Birsfelden, all of Switzerland

[73] Assignee: Ciba-Geigy Corporation, Ardsley, N.Y.

[22] Filed: May 7, 1975

[21] Appl. No.: 575,320

[30] Foreign Application Priority Data
May 10, 1974 Switzerland................ 6422/74

[52] U.S. Cl............. 424/274; 260/239 R; 260/239 BF; 260/268 R; 260/268 TR; 260/268 FT; 260/293.57; 260/293.68; 260/293.73; 260/326.34; 260/326.35; 260/326.43; 260/327 B; 260/332.2 R; 260/562 N; 424/250; 424/267; 424/275

[51] Int. Cl.²..................................... C07D 495/04

[58] Field of Search...... 260/327 B, 326.34, 293.57, 260/268 TR, 332.2 R; 424/275, 274, 267, 250

*Primary Examiner*—Henry R. Jiles
*Assistant Examiner*—Cecilia M. S. Jaisle
*Attorney, Agent, or Firm*—Joseph G. Kolodny; John J. Maitner; Theodore O. Groeger

[57] ABSTRACT

The invention relates to new aminoacyl compounds of the formula I,

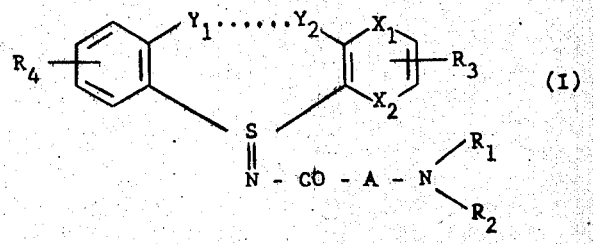

14 Claims, No Drawings

AMINOACYL COMPOUNDS

These new compounds possess valuable pharmacological properties. In particular they have an antidepressant and stimulant activity and can be used for the treatment of states of mental depression.

DETAILED DESCRIPTION

The present invention relates to new aminoacyl compounds, therapeutic preparations which contain the new compounds and the use thereof.

The compounds according to the invention correspond to the general formula I

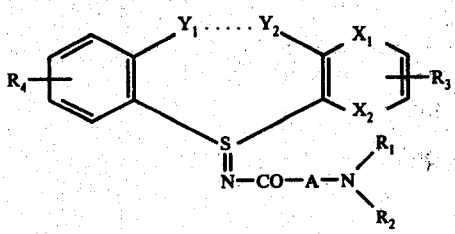

in which $R_1$ and $R_2$ denote hydrogen or lower alkyl groups or, conjointly with the adjacent N atom, denote an alkyleneimino group with 5 to 7 ring members, or a 1-piperazinyl or hexahydro- 1H-1,4-diazepin-1-yl group, which is optionally substituted in the 4-position by a lower alkyl group or a lower hydroxyalkyl group, $R_3$ denotes hydrogen, halogen up to atomic number 35 or a lower alkyl or alkoxy group, $R_4$ denotes hydrogen, halogen up to atomic number 35 or a lower alkyl, lower alkoxy, trifluoromethyl or nitro group, A denotes a divalent, saturated aliphatic hydrocarbon radical with 1 to 3 carbon atoms and one of the symbols $X_1$ and $X_2$ denotes a direct bond and the other denotes the vinylene group —CH=CH— or the epithio radical —S— and $Y_1$ and $Y_2$ denote hydrogen, or conjointly denote a divalent bridge member $Y_3$ of the following structure:

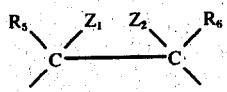

wherein $R_5$ and $R_6$ denote hydrogen or lower alkyl groups and $Z_1$ and $Z_2$ each denote hydrogen or conjointly denote an additional bond, or $R_5$ and $Z_1$ denote hydrogen and, at the same time, $R_6$ and $Z_2$ conjointly denote an oxo radical.

The addition salts of the compounds of the general formula I with inorganic or organic acids also form a subject of the invention.

In the compounds of the general formula I, $R_1$ and $R_2$, as lower alkyl groups, are those with 1 to 4 carbon atoms, such as the ethyl, propyl, isopropyl or butyl group, but preferably are methyl groups.

Conjointly with the adjacent nitrogen atom, $R_1$ and $R_2$, as the grouping —$NR_1R_2$, form the 1-pyrrolidinyl, piperidino, hexahydro-1H-azepin-1-yl, 1-piperazinyl or hexahydro-1H-1,4- diazepin-1-yl group. The two latter groups can be substituted in the 4-position, that is to say in the imino group, for example by an ethyl, propyl, isopropyl, butyl, isobutyl, 2- hydroxypropyl, 3-hydroxypropyl or 3-hydroxybutyl group and especially a methyl group or a 2-hydroxyethyl group.

$R_3$ and $R_4$, as halogen up to atomic number 35, are fluorine, chlorine or bromine and as lower alkyl groups or lower alkoxy groups are those with at most 7, and especially at most 4, carbon atoms, for example ethyl, propyl, isopropyl, butyl, isobutyl, tert.butyl, pentyl, isopentyl, 1,1-dimethylpropyl, 2,2-dimethylpropyl, hexyl, isohexyl or heptyl groups or above all methyl groups, or ethoxy, propoxy, isopropoxy, butoxy, isobutoxy, pentyloxy, isopentyloxy, 2,2-dimethylpropoxy, hexyloxy, isohexyloxy or heptyloxy groups and above all methoxy groups. $R_3$ is preferably hydrogen, fluorine or chlorine. $R_4$ is preferably hydrogen or bromine or the trifluoromethyl or nitro group and above all hydrogen, fluorine or chlorine.

Divalent, saturated aliphatic hydrocarbon radicals A are understood to be the methylene, ethylene, ethylidene, trimethylene and the propylidene group. The compounds of the general formula I are, on the one hand, when $Y_1$ and $Y_2$ denote hydrogen atoms, diphenylsulphilimine or phenyl-thienylsulphilimine derivatives and, on the other hand, insofar as $Y_1$ and $Y_2$ conjointly denote one of the bridge members $Y_3$ defined under general formula I, corresponding tricyclic compounds.

Lower alkyl groups which correspond to the meaning of $R_5$ and $R_6$ are those with 1 to 4 carbon atoms, for example ethyl, propyl, isopropyl or butyl groups and above all methyl groups.

The invention relates especially to compounds of the general formula I, in which $X_1$, $X_2$, $Y_1$ and $Y_2$ or $Y_3$ have the meaning indicated under general formula I, but wherein, in a bridge member ($Y_3$) formed from $Y_1$ and $Y_2$, $R_5$ and $R_6$, as alkyl groups, preferably denote methyl groups, $R_1$ and $R_2$ independently of one another denote hydrogen, lower alkyl groups with at most 4 carbon atoms or, conjointly with the adjacent nitrogen atom, an alkyleneimino group with 5 to 7 ring members or a 1-piperazinyl group, which is optionally substituted in the 4-position by a methyl or 2-hydroxyethyl group, $R_3$ denotes hydrogen, fluorine or chlorine and $R_4$ denotes hydrogen, fluorine or chlorine or a methyl, methoxy, trifluoromethyl or nitro group and A denotes the methylene or ethylene group. Within this group of compounds, those in which $R_1$ and $R_2$ independently of one another denote hydrogen or alkyl groups with at most 2 carbon atoms are of particular importance. The invention relates particularly to compounds of the general formula I, in which $X_1$ denotes a direct bond and $X_2$ denotes a vinylene radical or the epithio radical, $Y_1$ and $Y_2$ each denote hydrogen or conjointly, as $Y_3$, denote a bridge member of the structure indicated under formula I, in which $R_5$ and $R_6$ denote hydrogen or methyl groups and $Z_1$ and $Z_2$ denote hydrogen or conjointly denote an additional bond, $R_1$ and $R_2$ independently of one another denote hydrogen or alkyl groups with at most 2 carbon atoms, above all methyl groups, $R_3$ and $R_4$ independently of one another denote hydrogen, fluorine or chlorine and A denotes ethylene and above all methylene. Above all, the invention relates to compounds of the general formula I, in which $X_1$ and $X_2$ have the meaning indicated directly above and $Y_1$ and $Y_2$ each denote hydrogen or conjointly, as $Y_3$, denote a bridge member of the structure indicated under formula I, in which $R_5$ and $R_6$ denote hydrogen or methyl groups and $Z_1$ and $Z_2$ denote hydrogen or conjointly denote an additional bond, $R_1$ denotes a methyl group and $R_2$ denotes hydrogen or a methyl group, one of the symbols $R_3$ and $R_4$ denotes hydrogen and the other, preferably $R_4$, denotes chlorine or hydrogen, and A denotes a methylene group. Within this group of compounds, as also within the groups of compounds mentioned further above, those compounds in which $Y_1$ and $Y_2$ conjointly represent a bridge member $Y_3$ of the structure indicated under formula I, in which $R_5$ and $R_6$ and also $Z_1$ and $Z_2$ have the meaning indicated under formula I or the particular restricted meaning, are of particular importance.

The invention also relates in particular to the addition salts of the groups of compounds of the general formula I which have been singled out in the preceding text with inorganic and organic acids, above all the pharmaceutically acceptable acid addition salts.

Compounds in which the substitution characteristics mentioned in the preceding text are combined are, for example, N-(N-methylglycyl)-S,S-diphenylsulphilimine, N-(N,N- dimethylglycyl-β-alanyl)-S,S-diphenylsulphilimine, N-(N- methylglycyl)-S,S-bis-(p-fluorophenyl)-sulphilimine, 5,5- dihydro-5-[N-(N-methylglycyl)-imino]-dibenzo[b,f]thiepine, 5,5-dihydro-5-[N,(N,N-dimethylglycyl)-imino]-10,11-dimethyl-dibenzo[b,f]thiepine, 3-chloro-5,5-dihydro-5-[N-(N,N-dimethylglycyl) -imino]-dibenzo[b,f]thiepine, 5,5,10,11-tetrahydro- 5-[N-(N-methylglycyl)-imino]-dibenzo[b,f]thiepine, 10,10-dihydro-10-[N-(N,N-dimethylglycyl)-imino]-thieno[2,3-b]- [1]thiepine, 5,5,10,11-tetrahydro-5-[N-(N,N-dimethylglycyl)- imino]-dibenzo[b,f]thiepine, 2-chloro-5,5-dihydro-5-[N-(N,N- dimethylglycyl)-imino]-dibenzo[b,f]thiepine and 2-chloro- 5,5,10,11-tetrahydro-5-[N-(N,N-dimethylglycyl)-imino]- dibenzo[b,f]thiepine.

The compounds of the general formula I and the corresponding addition salts effective inorganic and organic acids possess valuable pharmacological properties. They have an antidepressant and stimulant action. The antidepressant activity can be determined, for example, by ascertaining the reserpine-antagonistic activity in the reserpine-ptosis test on mice using doses from about 40 mg/kg intraperitoneally, and also by examining the tetrabenazine-antagonistic activity in rats using doses from 20 to about 40 mg/kg perorally and by boosting the 5-hydroxy-tryptophane action in mice using doses from about 3 mg/kg perorally. The central-stimulant, especially the antidepressant, properties, which can be determined by selected standard tests [compare R. Domenjoz and W. Theobald, Arch. Int. Pharmacodyn, 120, 450 (1959) and also W. Theobald et al., Arzneimittelforsch. 17, 561 (1967)], characterise the compounds of the general formula I and their pharmaceutically acceptable addition salts with inorganic and organic acids as active substances for antidepressants and central stimulants, which, for example, can be used for treating states of depression and masked and endogenous depression.

The compounds of the general formula I and their acid addition salts are manufactured, according to the invention, by reacting a reactive ester of a compound of the general formula II

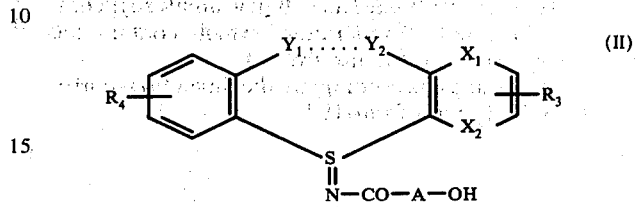

in which A, $R_3$, $R_4$, $X_1$, $X_2$, $Y_1$ and $Y_2$ have the meaning indicated under the general formula I, with a compound of the general formula III

wherein $R_1$ and $R_2$ have the meaning indicated under the general formula I, or with hexamethylenetetramine, and, if desired, converting the resulting compound of the general formula I into an addition salt with an inorganic or organic acid. In this reaction the reactive ester group is exchanged directly for the amino group corresponding to the compound of the general formula III, whilst the reaction product with hexamethylenetetramine is converted, by subsequent decomposition with a dilute mineral acid, for example hydrochloric acid, into a compound of the general formula I, in which $R_1$ and $R_2$ are hydrogen. Reactive esters in the indicated sense are, for example, the halides, say the chlorides and particularly the bromides and especially the iodides which are prepared from these in situ immediately prior to the reaction; the esters with methanesulphonic acid, o- and p-toluenesulphonic acid and o- and p-chlorobenzenesulphonic acid can also be used. Lower alkanols, for example methanol, ethanol, propanol, isopropanol and also butanol, are used as reaction media; however, lower fatty acid amides, such as, for example, dimethylformamide or mono- and dimethylacetamide and also acetonitrile, sulpholane, N,N,N,', N'-tetramethylurea or hexamethylphosphoric acid triamide or mixtures of the indicated solvents can also be employed advantageously. The reaction can be carried out at room temperature, but advantageously within a temperature range from 20° to 150° C, the rate of conversion being dependent to a clear extent on the nature of the amine of the formula III which is employed, on the one hand, and, on the other hand, on the solvent used and on the reaction temperature. The reaction of a reactive ester of the general formula II, preferably the chloride or bromide, with hexamethylenetetramine is carried out in an inert solvent, for example methylene chloride, chloroform, chlorobenzene or mixtures thereof, at room temperature or in a temperature range from 20° to 40° C by leaving to stand for several hours. This is followed by the decomposition of the reaction product with, for example, dilute hydrochloric acid, a compound of the general formula I, in which $R_1$ and $R_2$ denote hydrogen, being obtained.

Starting materials of the general formula II can be manufactured, for example, by reacting a compound of the general formula IV

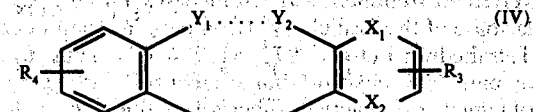

wherein $R_3$, $R_4$, $X_1$, $X_2$, $Y_1$ and $Y_2$ have the meaning indicated under general formula I, with a derivative of a carboxylic acid of the general formula IIa HOOC — A — OH     (IIa)

in which A has the meaning indicated under general formula I, the hydroxyl group is reactively esterified in the manner explained in more detail in the definition of the corresponding acyl radical, which is contained in general formula II, and, if appropriate, the carboxyl group is activated. The reaction can be carried out, for example, by heating the reactants with azeotropic removal of the water formed, advantageously in a solvent which forms azeotropic mixtures, such as, for example, butanol, benzene or xylene, or mixtures thereof, the presence of acid substances, for example concentrated sulphuric acid, benzenesulphonic acid or p-toluenesulphonic acid, being advantageous in some cases.

Carboxylic acids with a reactively modified carboxyl group are, for example, the halides, especially the chlorides, and also the azides and anhydrides and mixed anhydrides with a derivative of carbonic acid or phosphoric acid or with an organic acid, such as, for example, acetic acid, propionic acid and benzoic acid; the esters of such carboxylic acids, such as, say, the lower alkyl esters, say the methyl, ethyl, propyl, butyl or cyanomethyl ester, and also aralkyl esters, such as benzyl or p-nitrobenzyl esters, or aryl esters, especially, for example, the p-nitrophenyl ester, can also be used. The reaction media used are inert solvents, such as, say, on the one hand, chlorinated hydrocarbons, such as, for example, methylene chloride, chloroform, carbon tetrachloride, benzene or toluene, or mixtures thereof, advantageously in the presence of an acid-binding agent, insofar as substances having an acid reaction are formed during the reaction, or in the presence of an alkaline condensing agent, such as, say, sodium methylate, insofar as the reactions are carried out with esters of carboxylic acids.

The compounds of the general formula IV, which serve as starting materials, are new substances, with the exception of those compounds in which $X_1$ or $X_2$ denotes the vinylene group, $Y_1$ and $Y_2$ represent hydrogen and, at the same time, $R_3$ and $R_4$ either both denote hydrogen atoms or both denote methoxy groups, which are in the p-position relative to the sulphur atom, or one denotes hydrogen and the other denotes a methyl or nitro group, which is in the p-position relative to the sulphur atom, or a chlorine atom in the p-position.

The compounds of the general formula IV are manufactured by hydrolysis of compounds of the general formula IIb

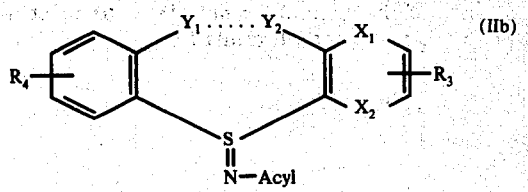

wherein Acyl denotes the acyl radical of an organic sulphonic acid or of a strong carboxylic acid and $R_3$, $R_4$, $X_1$, $X_2$, $Y_1$ and $Y_2$ have the meaning defined under general formula I.

Organic sulphonic acids are, for example, methanesulphonic acid, benzenesulphonic acid or o- and p-toluenesulphonic acid, mesitylenesulphonic acid, and also o- and p-chlorobenzenesulphonic acid as well as m-nitrobenzenesulphonic acid; strong carboxylic acids are understood to be especially halogenated alkanecarboxylic acids, such as, for example, the chlorinated acetic acids, namely dichloroacetic acid and trichloroacetic acid and also difluoroacetic acid and trifluoroacetic acid as well as dibromoacetic acid. The hydrolysis of the compounds of the general formula IIb is preferably carried out by treatment with strong acids, such as concentrated sulphuric acid, at room temperature, the bases of the general formula IV being liberated from the iminosulphonium salts, which are initially formed, by the action of aqueous alkalis.

The compounds of the general formula IIb, for their part, are manufactured by reacting a compound of the general formula IIc

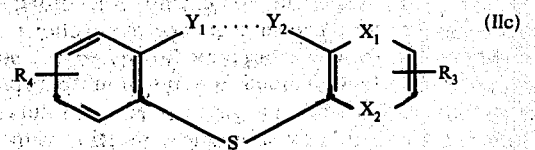

wherein $R_3$, $R_4$, $X_1$, $X_2$, $Y_1$ and $Y_2$ have the meaning indicated under general formula I, for example sodium N-chloro-p-toluenesulphonamide or other sodium compounds of N-chloroamides, by which means the corresponding N-(p-tolylsulphonyl)-sulphilimines or analogues with other corresponding acyl groups or analogous heterocyclic compounds are obtained.

The manufacture of compounds of the general formula IIb and their hydrolysis to give new compounds of the general formula IV can be carried out, for example, according to or analogously to the known manufacture of those compounds of the general formula IV, in which $Y_1$ and $Y_2$ represent hydrogen, $R_3$ denotes hydrogen and $R_4$ denotes hydrogen or chlorine or a methyl or nitro group in the p-position relative to the sulphur atom, from diphenyl sulphide or p-chloro-, p-methyl- or p-nitro-diphenyl sulphide. (Compare N. Furukawa et al., Tetrahedron Letters 1972, 1619–1622).

A further process for the manufacture of the compounds of the general formula IV is to react a compound of the general formula IId

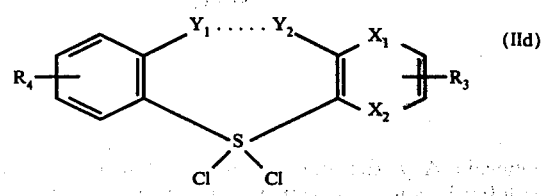

wherein $R_3$, $R_4$, $X_1$, $X_2$, $Y_1$ and $Y_2$ have the meaning defined under general formula I, with ammonia and to liberate a compound of the general formula IV from the chloride of this compound, which is initially formed, with the aid of a strong base.

To carry out this process, elemental chlorine is allowed to act on a compound of the general formula IIc, which has been explained above, the corresponding sulphidedichlorides or heterocyclic analogues of the general formula IId being obtained, which are converted, by subsequent reaction with liquid ammonia, into the corresponding sulphiliminium chlorides or their heterocyclic analogues. The corresponding free base of the formula IV can be obtained from these products, for example by treatment with a solution of sodium in liquid ammonia. The manufacture of the compounds of the general formula IId and their further reaction is carried out, for example, according to or analogously to a known sequence of reactions, in accordance with which bis(p-methoxyphenyl) sulphidedichloride is first obtained from bis-(p-methoxyphenyl) sulphide and dry chlorine gas in a benzene solution and is then converted, by subsequent reaction with liquid ammonia, into bis-(p-methoxyphenyl)-sulphiliminium chloride; bis-(p-methoxyphenyl)-sulphilimine can then be obtained from this by the action of sodium amide or of a solution of sodium in liquid ammonia. [Compare B. Appel, W. Büchner, Chem. Ber. 95, 2220–2224 (1962)].

In accordance with a further process, the compounds of the general formula IV are manufactured by reacting a compound of the general formula IIc, which has been defined further above, with a hydroxylamine derivative of the general formula IIe

wherein R denotes a hydroxyl group or a hydrocarbon radical which optionally carries one or more inert substituents, and liberating the compound of the general formula IV from the salt of this compound, which is initially formed, with the aid of a strong base. In this reaction the sulphonium salts of compounds of the general formula IV are first obtained and are converted, by treatment with strong bases, into the particular base of the formula IV. (Compare Y. Tamura et al., Tetrahedron Letters 1972, 4137–4140). Thus, for example, 5,5-dihydro-5-imino-dibenzo[b,f]thiepine is obtained by reacting dibenzo[b,f]thiepine with O-mesitylenesulphonyl hydroxylamine in methanol at room temperature and subsequently treating with a methanolic sodium methylate solution. Other compounds comprised by the general formula IV can be manufactured in an analogous manner, for example 5,5-dihydro-5-imino-10,11-dimethyl-dibenzo[b,f]thiepine from 10,11-dimethyl-dibenzo[b,f]thiepine.

According to a second process, the compounds of the general formula I and their acid addition salts are manufactured by reacting a compound of the formula IV

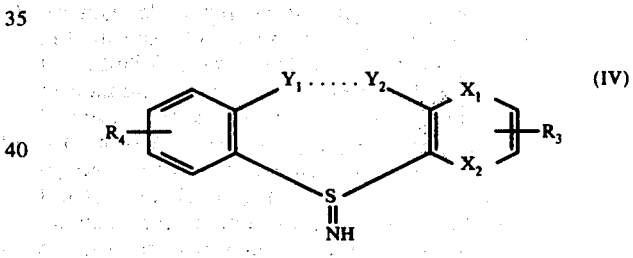

wherein $R_3$, $R_4$, $X_1$, $X_2$, $Y_1$ and $Y_2$ have the meaning indicated under formula I, with a carboxylic acid of the formula V

wherein A has the meaning indicated under formula I, D denotes hydrogen, a lower alkyl group or a protective group which can be replaced by hydrogen by means of hydrolysis, and E denotes a lower alkyl group or a protective group which can be replaced by hydrogen by means of hydrolysis, or D and E conjointly with the adjacent nitrogen atom denote an alkyleneimino group with 5 to 7 ring members, or a 1-piperazinyl group or hexahydro-1H-1,4-diazepin-1-yl group, which are optionally substituted in the 4-position by a lower alkyl or hydroxyalkyl group or by a protective group which can be replaced by hydrogen by means of solvolysis, subsequently, if necessary, hydrolysing a compound containing protective groups, which has thus been obtained, and, if desired, converting a resulting compound of the general formula I into an addition salt with an inorganic or organic acid.

In a starting material of the general formula V with a primary or secondary amino group, the latter is advantageously protected by any of the easily removable amino protective groups which are known in peptide chemistry. Such protective groups can be, for example, acyl, arylmethyl, 2-carbonyl-1-vinyl, arylthio or aryl-lower alkylthio and also arylsulphonyl as well as organic silyl or stannyl groups. The starting material of the formula V can also be used in the form of an acid addition salt, in which the amino group is protected in the ionic form.

An easily removable acyl group is, for example, the formyl group or the acyl radical of a half-ester of carbonic acid, such as a lower alkoxycarbonyl group, which is preferably aliphatically polysubstituted on the carbon atoms in the α-position to the hydroxyl group or is branched and/or aromatically or heteroaromatically substituted, or a methoxycarbonyl group, which is substituted by an arylcarbonyl radical, especially a benzoyl radical, or a lower alkoxycarbonyl group, which is substituted by halogen in the β-position, for example tert.butoxycarbonyl, tert.pentyloxycarbonyl, phenacyloxycarbonyl, 2,2,2-trichloroethoxycarbonyl or 2-iodoethoxycarbonyl or a group which can be converted into the latter, such as 2-chloroethoxycarbonyl or 2-bromoethoxycarbonyl, and also preferably polycyclic cycloalkoxycarbonyl, for example adamantyloxycarbonyl, phenyl-lower alkoxycarbonyl which is optionally substituted, for example by lower alkyl, hydroxyl, lower alkoxy or nitro, especially α-phenyllower alkoxycarbonyl, for example 4-methoxy-benzyloxy-carbonyl, 4-hydroxy-3,5-bis-tert.butyl-benzyloxycarbonyl, 4-nitrobenzyloxycarbonyl or α-4-biphenyl-α-methylethyloxycarbonyl, and also diphenylmethoxycarbonyl which is optionally substituted, for example by lower alkoxy, for example diphenylmethoxycarbonyl, or furyl-lower alkoxycarbonyl, above all α-furyl-lower alkoxycarbonyl, for example furfuryloxycarbonyl.

An acyl group to protect the amino group can also be the corresponding radical of a suitable carboxylic acid, such as the phthaloyl or trifluoroacetyl radical.

Easily removable arylmethyl groups to be singled out are, for example, optionally substituted polyarylmethyl groups, such as triarylmethyl groups, for example trityl which is optionally substituted by lower alkoxy, especially o- and/or p-methoxy-substituted trityl.

Easily removable 2-carbonyl-1-vinyl groups, which, conjointly with the amino group, form either an enamine or the ketimine which is tautomeric thereto, are, for example, 2-lower alkoxycarbonyl-1-lower alkylvinyl groups, especially the 2-methoxycarbonyl-1-methyl-1-vinyl group.

Easily removable arylthio or aryl-lower alkylthio groups are, for example, substituted phenylthio groups, for example phenylthio groups substituted by nitro or halogen, such as the o-nitrophenylthio, 2,4-dinitrophenylthio or pentachlorophenylthio group and also triarylmethylthio groups, for example the triphenylmethylthio group.

An easily removable organic silyl or stannyl group can carry as substituents preferably optionally substituted, especially aliphatic, hydrocarbon radicals, such as lower alkyl, for example methyl, ethyl or tert.butyl, or halogenolower alkyl, for example 2-chloroethyl, and also functional groups, for example etherified or esterified hydroxyl groups, such as lower alkoxy, for example methoxy or ethoxy, or halogen, for example chlorine. Silyl or stannyl radicals of this type are, amongst others, tri-lower alkylsilyl, for example trimethylsilyl or tert-.butyldimethylsilyl, lower alkoxy-lower alkyl-halogenosilyl, for example chloro-methoxymethyl-silyl, or tri-lower alkyl-stannyl, for example tri-n-butyl-stannyl.

If a free acid of the formula V, preferably with a protected or a tertiary amino group, is employed for the acylation of the imino group in a compound of the formula IV, suitable condensing agents, such as carbodiimides, for example N,N'-diethyl-, N,N'-dipropyl-, N,N'-diisopropyl-, N,N'-dicyclohexyl- or N-ethyl-N'-γ-dimethylaminopropylcarbodiimide, suitable carbonyl compounds, for example carbonyl-diimidazole, or isoxazolinium salts, for example N-ethyl-5-phenyl-isoxazolinium 3'-sulphonate and N-tert.butyl-5-methyl-isoxazolinium perchlorate, or an acylamino compound, for example 2-ethoxy-1-ethoxycarbonyl-1,2-dihydroquinoline, are customarily used.

The condensation reaction is preferably carried out in one of the anhydrous reaction media which are mentioned further below, for example in methylene chloride, dimethylformamide or acetonitrile.

A functional derivative of an acid of the formula IV, preferably with a protected amino group, which is suitable for the reaction according to the invention is, above all, an anhydride of such an acid, including the mixed anhydrides. Mixed anhydrides are, for example, those with inorganic acids, such as hydrogen halide acids, that is to say the corresponding acid halides, for example acid chlorides or acid bromides, and also with an acid containing phosphorus, for example phosphoric acid or phosphorous acid, or with an acid containing sulphur, for example sulphuric acid. Other mixed anhydrides are, for example, those with organic carboxylic acids, such as with lower alkanecarboxylic acids which are optionally substituted, for example by halogen, such as fluorine or chlorine, for example pivalic acid or trichloroacetic acid, or with lower alkyl half-esters of carbonic acid, such as the ethyl or isobutyl half-ester of carbonic acid, or with organic, in particular aliphatic or aromatic sulphonic acids, for example p-toluenesulphonic acid.

Further acid derivatives of an acid of the formula V which are suitable for reaction with the free imino group of a compound of the formula IV are activated esters, optionally with a protected amino group, such as for example, phenyl esters which are preferably substituted by nitro groups or halogen, such as chlorine, for example pentachlorophenyl or 4-nitrophenyl esters or 2,4-dinitrophenyl esters, heteroaromatic esters, such as benztriazole esters, for example 2-benztriazole esters, or diacylimino esters, such as succinylimino or phthalylimino esters, and also an azide of the acid of the formula V, wherein the amino group is preferably protected or tertiary.

A primary or secondary amino group in an acid of the formula V or in an acid derivative thereof is preferably in the protected form and an acid derivative can, if desired, be formed in situ. Thus, for example, a mixed anhydride is obtained by treating an acid of the formula V, or a suitable salt thereof, such as an ammonium salt, for example one derived from an organic amine, such as N-methylmorpholine, or a metal salt, with a suitable acid derivative, such as a corresponding acid halide of an optionally substituted lower alkanecarboxylic acid, for example with trichloroacetyl chloride, or with a half-ester of a carbonic acid half-halide, for example chloroformic acid ethyl ester or chloroformic acid isobutyl ester, and the mixed anhydride thus formed is used direct, that is to say without isolation and purification.

This process, for example using an anhydride or an acid halide, is advantageously carried out in the presence of an acid-binding agent, for example an organic base, such as an organic amine, for example a tertiary amine, such as a tri-lower alkylamine, for example triethylamine, or a N,N-di-lower alkyl-aniline, for example N,N-dimethylaniline, an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or an oxirane, for example a lower 1,2-alkylene oxide, such as ethylene oxide or propylene oxide.

The acylation on which this process is based can be carried out in an aqueous, or preferably a non-aqueous, solvent or solvent mixture, for example in a carboxylic acid amide, such as N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at a lowered or elevated temperature and/or in an inert gas atmosphere, for example a nitrogen atmosphere.

Any amino protective groups which may be present in a compound obtained by this process are replaced by hydrogen by means of solvolysis, the reaction conditions depending on the nature of the radicals to be split off. Thus, for example, a tert.butoxycarbonyl or diphenylmethoxycarbonyl group which serves as a protective group for the amino group in a resulting compound can be split off and replaced by hydrogen, for example by treatment with a suitable acid, such as trifluoroacetic acid, optionally in the presence of anisole. A formyl group, as an amino protective group, can be split off, for example by treatment with an acid agent, for example p-toluenesulphonic acid or hydrochloric acid, a weakly basic agent, for example dilute ammonia, or a decarbonylating agent, for example tris-(triphenylphosphine)rhodium chloride.

In a resulting compound an easily removable acyl group, group, such as an α-polybranched lower alkoxycarbonyl group, for example tert.butoxycarbonyl, and also a polycyclic cycloalkoxycarbonyl group, for example 1-adamantyloxycarbonyl, an optionally substituted diphenylmethoxycarbonyl group, for example diphenylmethoxycarbonyl, or an α-furyl-lower alkoxycarbonyl group, and also a 4-hydroxy-3,5-bis-tert.butylbenzyloxycarbonyl group, can be split off from an acylamino group, for example by treatment with a suitable acid, such as formic acid or trifluoroacetic acid, optionally in the presence of anisole. A phenacyloxycarbonyl group can also be split off by treatment with a suitable nucleophilic, preferably salt-forming, reagent, such as sodium thiophenolate.

A triarylmethyl group, such as the trityl group, can be split off, for example, by treatment with an acid agent, such as a mineral acid, for example hydrochloric acid.

An amino group which is protected in the form of an enamine or a ketimine which is tautomeric thereto, and also the amino groups protected by arylthio, aralkylthio and arylsulphonyl, which have been mentioned, can be liberated, for example by treatment with an acid agent, above all an aqueous acid, such as an organic carboxylic acid, for example formic acid, acetic acid or propionic acid, or a mineral acid, for example hydrochloric acid or sulphuric acid, optionally in the presence of a water-miscible solvent, such as a lower alkanol, for example methanol, a ketone, for example acetone, an ether, for example tetrahydrofurane, or also a nitrile, for example acetonitrile. The removal of the thio protective groups mentioned can be carried out particularly rapidly in the presence of additional reagents, such as sodium thiosulphate, thioacetamide, thiourea and potassium iodide.

An amino group protected with an organic silyl or stannyl group, in a resulting compound, can be liberated by treatment with an aqueous or alcoholic agent, for example with a lower alkanol, such as methanol, or a mixture thereof; the splitting of an amino group protected in this way usually already takes place during the working up of the acylation product.

The compounds, obtained by the process according to the invention, in which the amino group is substituted by a silyl or stannyl group are converted into compounds of the general formula I during working up, especially under hydrolytic and/or alcoholytic conditions, for example such as are customary in the removal of organic silyl or stannyl groups from amino groups.

The compounds, wherein the amino group is substituted by an ylidene group, which are obtained by the acylation, on which the process according to the invention is based, of compounds of the formula IV are converted into compounds of the general formula I during working up, especially by hydrolysis, for example by treatment with water.

The starting materials of the formula IV, which are required for this process, have been described after the first process.

Starting materials of the formula V are known from the literature and are accessible by known methods. In particular, starting materials of the formula V, or their reactive esters, can be converted into amino-protected compounds by treating, for example, N-methylglycine in an alkaline-aqueous solution with tert.butoxycarbonyl azide and, after acidification and the customary working up, isolating N-methyl-N-tert.butoxycarbonylglycine. Other acyl radicals can be introduced, as protective groups, into compounds of the formula V in an analogous manner. Furthermore, a triarylmethyl group can be introduced into the free amino group, for example by treatment with a reactive ester of a triarylmethanol, such as trityl chloride, preferably in the presence of a basic agent, such as pyridine.

The amino group can also be protected by introducing a silyl or stannyl group. Such groups are introduced in a manner which is in itself known, for example by treatment with a suitable silylating agent, such as a dihalogeno-di-lower alkyl-silane or tri-lower alkylsilyl halide, for example dichloro-dimethylsilane or trimethylsilyl chloride, or an optionally N-mono-lower alkylated, N,N-di-lower alkylated, N-tri-lower alkylsilylated or N-lower alkyl-N-tri-lower alkylsilylated N-(tri-lower alkylsilyl)-amine (see, for example, British Pat. No. 1,073,530), or with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, or a tri-lower alkyl-lower alkoxy-tin, tetra-lower alkoxy-tin or tetra-lower alkyl-tin compound, and also a tri-lower alkyl-tin halide, for example tri-n-butyl-tin chloride (see, for example, Netherlands Published Application 67/11,107).

The amino group can also be protected by introducing a 2-carbonyl-1-vinyl group, enamine or ketimine compounds being formed. Such groups can be obtained, for example, by treating the amine with a 1,3-dicarbonyl compound, for example with acetoacetic acid methyl ester or acetoacetic acid N,N-dimethylamide, in an anhydrous medium, for example a lower alkanol, such as methanol.

Arylthio or aryl-lower alkylthio and also arylsulphonyl protective groups can be introduced into an amino group by treatment with a corresponding arylsulphenyl or aryl-lower alkylsulphenyl halide or also an arylsulphonyl halide, for example a corresponding chloride.

Further starting materials which are derived from reactive functional derivatives of a compound of the formula V can be manufactured in a manner which is in itself known. Halides of such compounds are manufactured, for example, by reacting a compound of the formula V having an optionally protected amino group, or a salt thereof, with a halogenating agent, for example phosphorus pentachloride, thionyl chloride or oxalyl chloride. The reaction is preferably carried out in a non-aqueous solvent or solvent mixture, such as a carboxylic acid amide, for example dimethylformamide. The resulting acid halide does not need to be further purified but can be reacted direct with a compound of the formula IV, it being possible to use the same solvents or solvent mixtures which can be used for the manufacture of the acid halide.

Symmetrical or mixed anhydrides of compounds of the formula V having an optionally protected amino group can be manufactured, for example, by reacting a corresponding compound having a free carboxyl group, preferably a salt, especially an alkali metal salt, for example a sodium salt or ammonium salt, for example the triethylammonium salt thereof, with a reactive derivative, such as a halide, for example the chloride, of one of the acids mentioned, for example a lower alkyl halogenoformate or a lower alkanecarboxylic acid chloride.

Activated esters of compounds of the formula V having an optionally protected amino group can be manufactured, for example, by reacting a corresponding compound having a free carboxyl group, in the presence of a carbodiimide, for example one of the carbodiimides mentioned further above, such as N,N'-dicyclohexylcarbodiimide, with a phenol which is optionally substituted, for example by nitro or halogen, such as chlorine, such as, inter alia, nitrophenol, for example 4-nitrophenol or 2,4-dinitrophenol, or polyhalogenophenol, for example 2,3,4,5,6-pentachlorophenol.

In accordance with a third process, the compounds of the general formula I and their acid addition salts are manufactured by subjecting a compound of the formula VI

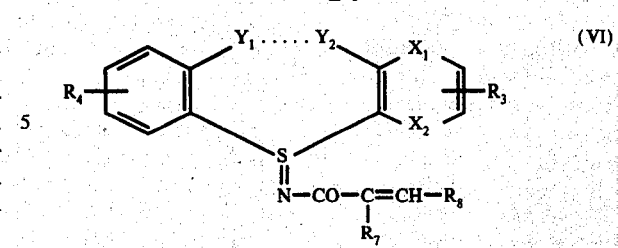

in which $R_7$ and $R_8$ independently of one another denote hydrogen or methyl groups and $X_1$, $X_2$, $Y_1$, $Y_2$, $R_3$ and $R_4$ have the meaning indicated under formula I, to an addition reaction with an amine of the general formula III, which has been mentioned previously, in which $R_1$ and $R_2$ have the meaning indicated under formula I, and, if desired, converting a resulting compound of the general formula I into an addition salt with an inorganic or organic acid.

In addition to ammonia, preferably primary amines, such as, for example, methylamine, ethylamine, propylamine, isopropylamine and butylamine, and also secondary amines are employed as amines of the formula III for the reaction according to the invention.

The reaction is preferably carried out with those compounds of the formula VI wherein $R_8$ represents hydrogen or the methyl group and $R_7$ denotes hydrogen. The diluents of the formula III is preferably employed in excess in the reaction according to the invention; the molar ratio of a compound of the formula VI to the amine of the formula III comprises the range from 1:1 to 1:3.5. Within this range, depending on the structure and reactivity of the reactants, a molar ratio of 1:1 to 1:1.8, and preferably a molar ratio from 1:1 to 1:1.2, is selected. The process is carried out in the presence or absence of solvents. The use of solvents or dilutents can be unnecessary, especially when the amine employed is liquid. If both reactants are solid, solvents are preferably employed, which can be, for example, water, a lower alkanol, for example methanol, ethanol, propanol, isopropanol or butanol, or also an ether-like medium, such as, for example, tetrahydrofurane or dioxane, the two lastmentioned, either in the anhydrous form or as mixtures with water, as well as benzene.

The process according to the invention is carried out in a temperature range from 0° to 100° C and, under certain circumstances, in a closed vessel. Depending on the reactivity and the properties of the reactants, especially the amines of the formula III, a temperature range of 10°–85° C is preferred; within this range in turn, depending on the reactivity of the components, a temperature interval of 15°–60° C is preferably employed. This can be of advantage, for example, when lower primary or secondary amines are employed, with which the reaction in some cases already takes place at room temperature.

A particularly preferred embodiment of this process comprises the use of gentle conditions, which comprise, on the one hand, the use of lower reaction temperatures within the indicated intervals and, on the other hand, reaction times which meet this requirement and which should preferably be as short as possible.

Depending on the reactivity of the components employed and the reaction temperature used, the reaction time is about one hour to 7 days.

Gentle conditions for carrying out the reaction according to the invention comprise, for example, leaving the reaction batch containing the components to stand for 1 to 3 hours at room temperature and subsequently heating it to about 50°–70° C for about 2 further hours. Under certain circumstances it is advisable or even necessary to employ a compound of the formula VI in the stabilised form, which is effected by the addition of small amounts of stabilisers. Substances of this type which have a stabilising action are, for example, derivatives of phenol and its polyhydroxylated analogues as well as the ring-alkylated derivatives thereof, such as, for example, 2,4,6-tri-tert.butylphenol, resorcinol and hydroquinone as well as the lower monoalkyl ethers thereof, such as resorcinol monomethyl ether, resorcinol monopropyl ether, hydroquinone monomethyl ether and hydroquinone monopropyl ether, pyrogallol as well as the lower monoalkyl ethers thereof, lower alkyl esters of mono- and polyhydroxybenzoic acids, for example p-hydroxybenzoic acid methyl ester or p-hydroxybenzoic acid propyl ester, gallic acid propyl ester as well as mixtures of stabilisers of the abovementioned type. The stabilisers of this type are employed, if appropriate, in amounts of 0.01 – 0.5%, preferably 0.05 – 0.2%, relative to the amount of a compound of the formula VI which is employed.

Starting materials of the formula VI are accessible, for example, by reacting a compound of the formula IV, wherein $R_3$, $R_4$, $X_1$, $X_2$, $Y_1$ and $Y_2$ have the meaning indicated there, with a carboxylic acid of the formula VIa

wherein $R_7$ and $R_8$ have the meanings indicated under formula VI, or a reactive functional derivative thereof. The methods which can be used for this purpose are mainly those which enable the acylation, on which the process is based, to be carried out under gentle conditions.

To carry out this process, for example, a carboxylic acid of the formula VI, which is stabilised, if appropriate, by the addition of a substance having a stabilising action, is reacted with a compound of the formula IV, in the presence of a carbodiimide, such as, for example, dicyclohexylcarbodiimide, in an inert solvent, such as, for example, tetrahydrofurane or dioxane, optionally in a mixture with water. Lower alkyl esters, such as, for example, the methyl esters or ethyl esters of the carboxylic acids of the general formula VIa, can be reacted even in the cold or, if necessary, with warming and, if appropriate, in a closed vessel, with compounds of the general formula IV to give the corresponding compounds of the general formula VI.

Other suitable reactive functional derivatives of carboxylic acids of the general formula VIa are the halides, especially the chlorides, and anhydrides, especially the mixed anhydrides with carbonic acid half-esters. These functional derivatives are reacted, if appropriate in the stabilised form, with a compound of the general formula IV, preferably in the presence of an acid-binding agent, for example a strong tertiary organic base, such as triethylamine, N-ethyl-diisopropylamine, pyridine or s-collidine, which in excess can also serve as the reaction medium, in the presence or absence of an inert organic solvent, such as, for example, dioxane, tetrahydrofurane, benzene or dimethylformamide. Other derivatives of the carboxylic acids of the general formula VIa which can be used are, for example, the p-nitro-phenyl esters and cyano-methyl esters thereof, which are reacted with compounds of the general formula VI in inert organic solvents, if necessary with warming. Under analogous conditions, the 1-imidazolides of the carboxylic acids of the general formula VIa are reacted with compounds of the general formula IV.

If desired, a compound of the general formula I, in which $R_1$ and/or $R_2$ denotes hydrogen, is converted into the corresponding compound of the general formula I, in which $R_1$ and $R_2$ denote alkyl groups. This can be effected in particular by reductive alkylation. To carry out this alkylation, for example, an aliphatic oxo compound having 1 to 3 carbon atoms is reacted with a compound of the general formula I of the indicated type and the reaction product is reduced in situ, formic acid at the boiling point of the reaction mixture advantageously being employed as the reducing agent. However, the introduction of alkyl radicals $R_1$ and/or $R_2$ can also be effected by reaction with a reactive ester of a corresponding lower alkanol in the presence or absence of a basic condensing agent, such as, for example, sodium carbonate, potassium carbonate, triethylamine or N-ethyl-N,N-diisopropylamine. Reactive esters of corresponding lower alkanols which can be used are, for example, the chlorides and especially the bromides and iodides but also the esters with sulphuric acid and with organic sulphonic acids, for example with methanesulphonic acid, o- and p-toluenesulphonic acid as well as o- and p-chlorobenzenesulphonic acid.

The present invention also relates to those modifications of the processes mentioned, and their preliminary stages, in which a process is discontinued at any stage or in which a compound occurring at any stage as an intermediate product is used as a starting material and the missing steps are carried out, or a starting material is formed under the reaction conditions or optionally is used in the form of citric salt. If the salicylic starting materials are optically active, both the racemates and the isolated antipodes or, if diastereomerism exists, either racemate mixtures or specific racemates or also isolated antipodes can be employed. Starting materials of this type can also optionally be used in the form of salts.

Insofar as end substances are obtained as racemates or racemate mixtures, these can be separated, if desired, within the scope of the present invention, and resolved into their antipodes.

If desired, compounds of the general formula I obtained by the processes according to the invention are converted, in a customary manner into their addition salts with inorganic and organic acids. For example, hydrochloric acid, hydrobromic acid, sulphuric acid, phosphoric acid, perchloric acid, acid, methanesulphonic acid, ethanesulphonic acid, acetic acid, lactic acid, succinic acid, fumaric acid, maleic acid, malic acid, tartaric acid, citric acid, benzoic acid, salicylic acid, phenylacetic acid, mandelic acid or embonic acid are used for salt formation, preferably in the presence of a solvent, such as, for example, acetone, methanol, ethanol, ether or mixtures thereof.

Preferably pharmaceutically acceptable acid addition salts are manufactured but other acid addition salts, such as, for example, oxalates, can also be of importance when, for example, they crystallise well and are therefore suitable for the separation, purification and, if appropriate, storage of the reaction products which are finally used as free bases or in the form of other, pharmaceutically acceptable, acid addition salts.

The compounds of the general formula I and the corresponding pharmaceutically acceptable acid addition salts are preferably administered perorally or rectally. The daily doses vary between 0.10 and 10 mg/kg for warm-blooded animals. Suitable dosage units, such as dragees, tablets or suppositories, preferably contain 0.5 to 50 mg of an active substance according to the invention, that is to say a compound of the general formula I or a pharmaceutically acceptable acid addition salt of these substances. To manufacture the dosage units, the active substance is combined with solid pulverulent excipients, such as lactose, sucrose, sorbitol or mannitol; starches, such as potato starch, maize starch or amylopectin, and also laminaria powder or citrus pulp powder; cellulose derivatives or gelatine, optionally with the addition of lubricants, such as magnesium stearate or calcium stearate or polyethylene glycols, to give tablets or to give dragee cores. The latter are coated, for example, with concentrated sugar solutions, which, for example, can also contain gum arabic, talc and/or titanium dioxide, or with a lacquer which is dissolved in readily volatile organic solvents or solvent mixtures. Colorants can be added to these coatings, for example for characterising different doses of active substance. Other suitable oral dosage units are push-fit capsules made of gelatine as well as soft, sealed capsules made of gelatine and a plasticiser, such as glycerol. The former contain the active substance, preferably as granules, in a mixture with lubricants, such as talc or magnesium stearate, and optionally contain stabilisers, such as sodium metabisulphite or ascorbic acid.

The instructions which follow are intended to illustrate the manufacture of tablets, dragees and suppositories in more detail:

a. 150.0 g of 5,5-dihydro-5-[N-(N-methylglycyl)imino]-dibenzo[b,f]thiepine hydrochloride are mixed with 500 g of lactose and 292 g of potato starch and the mixture is moistened with an alcoholic solution of 8 g of gelatine and granulated through a sieve. After drying, 60 g of potato starch, 60 g of talc, 10 g of magnesium stearate and 20 g of highly disperse silicon dioxide are mixed in and the mixture is pressed to give 10,000 tablets, each 115 mg in weight and each containing 15 mg of active substance, which, if desired, can be provided with dividing grooves for finer adjustment of the dosage.

b. 12.5 g of 5,5-dihydro-5-[N-(N-methylgycyl)imino]-dibenzo[b,f]thiepine hydrochloride are mixed well with 16 g of maize starch and 6 g of highly disperse silicon dioxide. The mixture is moistened with a solution of 2 g of stearic acid, 6 g of ethylcellulose and 6 g of stearin in about 70 ml of isopropyl alcohol and granulated through a III sieve (Ph. Helv. V). The granules are dried for about 14 hours and then forced through a III–IIIa sieve. The granules are then mixed with 16 g of maize starch, 16 g of talc and 2 g of magnesium stearate and pressed to give 1,000 dragee cores. These are coated with a concentrated syrup of 2 g of shellac, 7.5 g of gum arabic, 0.15 g of colorant, 2 g of highly disperse silicon dioxide, 25 g of talc and 53.35 g of sugar and dried. The resulting dragees each weigh 172.5 mg and each contain 12.5 mg of active substance.

c. 25.0 g of 5,5-dihydro-5-[N-(N-methylglycol)imino]-dibenzo[b,f]thiepine hydrochloride and 1975 g of finely ground suppository base material (for example cacao butter) are mixed thoroughly and then melted. 1,000 2 g suppositories are cast from the melt, which is kept homogeneous by stirring. They each contain 25 mg of active substance.

d. 25.0 g of 5,5-dihydro-5-[N-(N-methylglycyl)imino]-dibenzo[b,f]thiepine hydrochloride are dissolved in 1 liter of twice distilled pyrogen-free water and the solution is filled into 1,000 ampoules and sterilised. One ampoule contains a 2.5% strength solution of 25 mg of active substance.

The examples which follow illustrate in more detail the manufacture of the new compounds of the general formula I and of starting materials not hitherto known, but are not intended to restrict the scope of the invention in any way.

EXAMPLE 1 a. 180 ml (0.9 mol) of a 15% strength methanolic monomethylamine solution are added dropwise at room temperature, whilst stirring, to a solution of 24 g (0.09 mol) of N-(chloroacetyl)-S,S-diphenylsulphilimine in 250 ml of benzene. The solution is then boiled for 48 hours under reflux, cooled and washed once with 50 ml of water and the organic phase is extracted exhaustively with 2 N hydrochloric acid. The combined extracts are rendered alkaline with concentrated sodium hydroxide solution, whilst cooling, and are extracted exhaustively with benzene. The combined benzene phases are dried over sodium sulphate and concentrated in vacuo. An oil, which is N-(N-methylglycyl)-S,S-diphenylsulphilimine, remains as a residue.

16 g (0.059 mol) of the resulting base are dissolved in 100 ml of acetone, the solution is cooled to 10° C and a solution of 5.4 g (0.06 mol) of oxalic acid in 10 ml of acetone is added. The resulting oxalate is purified by recrystallisation from ethanol; melting point 173°–174° C.

N-(Chloroacetyl)-S,S-diphenylsulphilimine, which is required as the starting product, is, for example, manufactured as follows:

b. A solution of 19.2 g (0.19 mol) of triethylamine in 50 ml of methylene chloride is added dropwise at room temperature, whilst stirring to a solution of 19 g (0.095 mol) of S,S-diphenylsulphilimine [compare Furukawa et al., Univ. Osaka: Tetrahedron Letters 1972, 1619–1622; Tamura et al., Univ. Osaka: Tetrahedron Letters 1972, 4137–4140] in 120 ml of methylene chloride and subsequently, whilst cooling slightly, a solution of 12.3 g (0.11 mol) of chloroacetyl chloride in 80 ml of methylene chloride is added dropwise. The mixture is stirred overnight at room temperature, the solvent is stripped off in vacuo, the residue is taken up in methylene chloride and the organic phase is washed with water until neutral. The product is then dried over sodium sulphate and the solution is evaporated in vacuo. N-(Chloroacetyl)-S,S-diphenylsulphilimine is obtained as an oily residue and is further processed as the crude product.

EXAMPLE 2 a. Analogously to Example 1 a), N-(N,N-dimethyl-β-alanyl)-S,S-diphenylsulphilimine is obtained in an oily form from 8.5 g (0.03 mol) of N-(3-chloropropionyl)-S,S-diphenylsulphilimine and 4.1 g (0.09 mol) of dimethylamine.

11 g (0.037 mol) of the resulting base and 3.3 g (0.037 mol) of oxalic acid give 14 g of oxalate, which is recrystallized from isopropanol; melting point 147°–148° C.

N-(3-Chloropropionyl)-S,S-diphenylsulphilimine, which is required as the starting product, is obtained, for example, as follows:

b. Analogously to Example 1 b), N-(3-chloropropionyl)-S,S-diphenylsulphilimine is obtained as an oil from 15 g (0.075 mol) of S,S-diphenylsulphilimine and 10.5 g (0.083 mol) of 3-chloropropionic acid chloride.

EXAMPLE 3 a. Analogously to Example 1 a), N-(N-methylglycyl)-S,S-bis-(p-fluorophenyl)-sulphilimine is obtained from 28.22 g (0.09 mol) of N-(chloroacetyl)-S,S-bis-(p-fluorophenyl)-sulphilimine and 180 ml (0.9 mol) of a 15% strength methanolic monomethylamine solution.

N-(Chloroacetyl)-S,S-bis-(p-fluorophenyl)-sulphilimine, which is required as the starting product, is obtained, for example, as follows:

b. Analogously to Example 1 b), N-(chloroacetyl)-S,S-bis-(p-fluorophenyl)-sulphilimine is obtained from 22.52 g (0.095 mol) of S,S-bis-(p-fluorophenyl)-sulphilimine and 12.3 g (0.11 mol) of chloroacetyl chloride.

Bis-(p-fluorophenyl)-sulphilimine, which in turn is required for this reaction, can be prepared, for example, as follows:

15.2 g (0.071 mol) of freshly prepared O-mesitylenesulphonyl-hydroxylamine are added to a solution of 13.0 g (0.059 mol) of bis-(p-fluorophenyl) sulphide in 200 ml of methylene chloride and the mixture is stirred for 15 hours at room temperature. A solution of 1.6 g (0.07 gram atom) of sodium in 30 ml of methanol is then allowed to drop into the mixture, which is kept at a temperature of 0°–5° C, and the reaction mixture is then extracted with three times 50 ml of water; the methylene chloride phase is separated off, dried over sodium sulphate and evaporated to dryness.

Crude S,S-bis-(p-fluorophenyl)-sulphilimine, which solidifies on prolonged standing, is obtained as a residue. It is purified by recrystallising from petroleum ether; melting point 39°–41° C.

EXAMPLE 4 a. 66 ml (0.33 mol) of a 15% strength methanolic monomethylamine solution are added dropwise at room temperature, whilst stirring, to a solution of 20 g (0.066 mol) of 5,5-dihydro-5-[N-(chloroacetyl)-imino]-dibenzo[b,f]thiepine in 250 ml of benzene. The solution is then boiled under reflux for 48 hours, cooled and washed once with 50 ml of water and the organic phase is extracted exhaustively with 2 N hydrochloric acid. The combined extracts are rendered alkaline with concentrated sodium hydroxide solution, whilst cooling, and extracted exhaustively with benzene. The combined benzene phases are dried over sodium sulphate and concentrated in a waterjet vacuum. An oil, which is 5,5-dihydro-5-[N-(N-methylglycyl)-imino]-dibenzo[b,f]thiepine, remains as a residue.

10 g (0.034 mol) of the resulting base are dissolved in 100 ml of acetone, the solution is cooled to 10° C and a solution of 3.1 g (0.034 mol) of oxalic acid in 10 ml of acetone is added. The oxalate is purified by recrystallising from methanol; melting point 220° C (decomposition).

5,5-Dihydro-5-[N-(chloroacetyl)-imino]-dibenzo[b,f]thiepine, which is employed as the starting product, is obtained, for example, as follows:

b. 12 g (0.057 mol) of O-mesitylenesulphonylhydroxylamine (compare Y. Tamura, K. Sumoto, J. Minamikawa and M. Ikeda, Tetrahedron Letters 1972, 4133) are added, at room temperature and whilst stirring, to a solution of 10 g (0.0475 mol) of dibenzo[b,f]-thiepine in 600 ml of methanol. The reaction solution is stirred overnight at room temperature, concentrated in a waterjet vacuum, taken up in 300 ml of methylene chloride and treated with a methanolic sodium methylate solution, which is prepared by dissolving 1.32 g (0.057 gram atom) of sodium in 25 ml of methanol. The solution is stirred for 10 minutes at room temperature and is then washed in a separating funnel with three times 100 ml of water. The solution is then dried over sodium sulphate and evaporated in a waterjet vacuum, an oil, which crystallises on prolonged standing, remains as a residue. 5,5-Dihydro-5-imino-dibenzo[b,f]thiepine is obtained by recrystallisation from methanol; melting point 124° C.

1.058 g (0.0047 mol) of the crude base are dissolved in 10 ml of acetone and the solution is neutralised accurately with 5 N ethanolic hydrochloric acid. The hydrochloride is precipitated by adding ether and is recrystallised from ethanol; melting point 265° C (decomposition).

c. A solution of 13.6 g (0.134 mol) of triethylamine in 50 ml of methylene chloride is added dropwise at room temperature, whilst stirring, to a solution of 15 g (0.067 mol) of 5,5-dihydro-5-imino-dibenzo[b,f]thiepine in 200 ml of methylene chloride and subsequently, whilst cooling slightly, a solution of 8.6 g (0.076 mol) of chloroacetyl chloride in 50 ml of methylene chloride is added dropwise. The mixture is stirred overnight at room temperature, the solvent is evaporated in a waterjet vacuum, the residue is taken up in methylene chloride and the organic phase is washed with water until neutral. The solution is then dried over sodium sulphate and evaporated in a waterjet vacuum. An oil, which is 5,5-dihydro-5-[N-(chloroacetyl)imino]-dibenzo[b,f]thiepine, remains as a residue and is further processed as the crude product.

EXAMPLE 5 a. Analogously to Example 4 a), 5,5-dihydro-5-[N-(N,N-dimethylglycyl)-imino]-10,11-dimethyl-dibenzo[b,f]thiepine is obtained as an oil from 11 g (0.033 mol) of 5,5-dihydro-5-[N-(chloroacetyl)-imino]-10,11-dimethyl-dibenzo[b,f]thiepine and 3.4 g (0.073 mol) of dimethylamine and is further processed as the crude product.

6 g (0.0178 mol) of the base and 1.6 g (0.0178 mol) of oxalic acid give the oxalate, which is purified by recrystallisation from methanol; melting point 212° C.

5,5-Dihydro-5-[N-(chloroacetyl)-imino]-10,11-dimethyl-dibenzo[b,f]thiepine, which is employed as the starting product, can be prepared, for example, in the following manner:

b. Analogously to Example 4 b), 5,5-dihydro-5-imino-10,11-dimethyl-dibenzo[b,f]thiepine is obtained as an oil from 13 g (0.54 mol) of 10,11-dimethyl-dibenzo[b,f]thiepine and 14 g (0.065 mol) of O-mesitylenesulphonylhydroxylamine and is characterised as the monohydrochloride; melting point 275° C (decomposition).

c. Analogously to Example 4 c), 5,5-dihydro-5-[N-(chloroacetyl)-imino]-10,11-dimethyl-dibenzo[b,f]thiepine is obtained as an oil from 10 g (0.0395 mol) of 5,5-dihydro-5-imino-10,11-dimethyl-dibenzo[b,f]thiepine and 5.2 g (0.046 mol) of chloroacetyl chloride and is further processed as the crude product.

EXAMPLE 6 a. Analogously to Example 4 a), 3-chloro-5,5-dihydro-5-[N-(N,N-dimethylglycyl)-imino]-dibenzo[b,f]thiepine is obtained as a colourless oil from 10.1 g (0.028 mol) of 3-chloro-5,5-dihydro-5-[N-(chloroacetyl)-imino]-dibenzo[b,f]thiepine and 150 ml of a 20% strength solution of dimethylamine in benzene.

The hydrochloride is obtained from the base analogously to Example 4 b); melting point 220° C (decomposition).

3-Chloro-5,5-dihydro-5-[N-(chloroacetyl)-imino]-dibenzo[b,f]thiepine, which is employed as the starting product, can be prepared, for example, in the following manner:

b. Analogously to Example 4 b), 3-chloro-5,5-dihydro-5-imino-dibenzo[b,f]thiepine of melting point 125°–129° C is obtained from 8.0 g (0.033 mol) of 3-chloro-dibenzo[b,f]thiepine and 9.2 g (0.043 mol) of O-mesitylenesulphonylhydroxylamine; melting point of the hydrochloride 265° C (decomposition).

c. Analogously to Example 4 c), 3-chloro-5,5-dihydro-5-[N-(chloroacetyl)-imino]-dibenzo[b,f]thiepine of melting point 196°–198° C is obtained from 7.8 g (0.028 mol) of 3-chloro-5,5-dihydro-5-imino-dibenzo[b,f]thiepine, 5.7 g (0.056 mol) of triethylamine and 6.2 g (0.031 mol) of chloroacetyl chloride.

EXAMPLE 7 a. Analogously to Example 4 a), 5,5,10,11-tetrahydro-5-[N-(N-methylglycyl)-imino]-dibenzo[b,f]thiepine is obtained from 20.03 g (0.066 mol) of 5,5,10,11-tetrahydro-5-[N-(chloroacetyl)-imino]-dibenzo[b,f]thiepine and 66 ml (0.33 mol) of a 15% strength methanolic monomethylamine solution.

5,5,10,11-Tetrahydro-5-[N-(chloroacetyl)-imino]-dibenzo[b,f]thiepine, which is employed as the starting material, can be prepared, for example, in the following manner:

b. Analogously to Example 4 b), 5,5,10,11-tetrahydro-5-imino-dibenzo[b,f]thiepine of melting point 104°–107° C is obtained from 8.05 g (0.038 mol) of 10,11-dihydro-dibenzo[b,f]thiepine and 10.2 g (0.047 mol) of O-mesitylenesulphonyl-hydroxylamine; melting point of the hydrochloride 255° C (decomposition).

c. Analogously to Example 4 c), 5,5,10,11-tetrahydro-5-[N-(chloroacetyl)-imino]-dibenzo[b,f]thiepine is obtained from 15.2 g (0.067 mol) of 5,5,10,11-tetrahydro-5-imino-dibenzo[b,f]thiepine, 13.6 g (0.134 mol) of triethylamine and 8.6 g (0.076 mol) of chloroacetyl chloride.

EXAMPLE 8 a. Analogously to Example 5 a), 10,10-dihydro-10-[N-(N,N-dimethylglycyl)-imino]-thieno[2,3-b][1]benzothiepine is obtained from 10.15 g (0.033 mol) of 10,10-dihydro-10-[N-(chloroacetyl)-imino]-thieno[2,3-b][1]benzothiepine and 3.4 g (0.073 mol) of dimethylamine.

10,10-Dihydro-10-[N-(chloroacetyl)-imino]-thieno[2,3-b][1]benzothiepine, which is employed as the starting product, can be prepared, for example, as follows:

Analogously to Example 4 b), 10,10-dihydro-10-imino-thieno[2,3-b][1]benzothiepine is obtained as an oil from 8.1 g (0.037 mol) of thieno[2,3-b][1]benzothiepine and 9.6 g (0.044 mol) of O-mesitylenesulphonyl-hydroxylamine and is characterised as the hydrochloride; melting point 205° C (decomposition).

Analogously to Example 4 c), 10,10-dihydro-10-[N-(chloroacetyl)-imino]-thieno[2,3-b][1]benzothiepine is obtained from 11.1 g (0.0395 mol) of 10,10-dihydro-10-iminothieno[2,3-b][1]benzothiepine and 5.2 g (0.046 mol) of chloroacetyl chloride.

EXAMPLE 9

Analogously to Example 7 a), crude 5,5,10,11-tetrahydro-5-[N-(N,N-dimethylglycyl)-imino]-dibenzo[b,f]thiepine of melting point 112°–116° C is obtained from 14.8 g (0.0487 mol) of 5,5,10,11-tetrahydro-5-[N-(chloroacetyl)-imino]-dibenzo[b,f]thiepine and 50 ml of a 20% strength solution of dimethylamine in benzene.

12.2 g of the crude base (0.0391 mol) and 3.52 g (0.0391 mol) of oxalic acid give the oxalate, which is purified by recrystallization from ethanol/ethyl acetate; melting point 208°–209° C.

EXAMPLE 10 a. Analogously to Example 4 a), crude 2-chloro-5,5-dihydro-5-[N-(N,N-dimethylglycyl)-imino]-dibenzo[b,f]thiepine is obtained as a viscous oil from 8.0 g (0.0238 mol) of 2-chloro-5,5-dihydro-5-[N-(chloroacetyl)-imino]-dibenzo[b,f]thiepine and 4.5 g (0.1 mol) of dimethylamine in 100 ml of benzene.

The oxalate is prepared from 8.0 g (0.0231 mol) of the crude base and 2.08 g (0.0231 mol) of oxalic acid in ethanol/ethyl acetate. The pure oxalate is obtained after recrystallisation from ethanol/ethyl acetate; melting point 202°–203° C.

2-Chloro-5,5-dihydro-5-[N-(chloroacetyl)-imino]-dibenzo[b,f]thiepine, which is employed as the starting material, is obtained in the following manner:

b. Analogously to Example 4 b), 2-chloro-5,5-dihydro-5-imino-dibenzo[b,f]thiepine is obtained from 24.2 g (0.1 mol) of 2-chlorodibenzo[b,f]thiepine and 25.8 g (0.12 mol) of O-mesitylenesulphonyl-hydroxylamine; melting point 116°–117° C (from benzene/petroleum ether). The resulting base is dissolved in ethanol and ethanolic hydrochloric acid is added until the mixture gives an acid reaction and the resulting hydrochloride is recrystallised from ethanol/ethyl acetate; melting point 230°–232° C.

c. Analogously to Example 4 c), 2-chloro-5,5-dihydro-5-[N-(chloroacetyl)-imino]-dibenzo[b,f]thiepine is obtained from 12.95 g (0.050 mol) of 2-chloro-5,5-dihydro-5-iminodibenzo[b,f]thiepine and 6.5 g (0.058 mol) of chloroacetyl chloride; melting point 166°–168° C (from benzene/petroleum ether).

EXAMPLE 11 a. Analogously to Example 4 a), 2-chloro-5,5,10,11-tetrahydro-5-[N,N-dimethylglycyl)-imino]-dibenzo[b,f]thiepine is obtained as an oil from 16.9 g (0.050 mol) of 2-chloro-5,5,10,11-tetrahydro-5-[N-(chloroacetyl)-imino]-dibenzo[b,f]thiepine and 9.0 g (0.2 mol) of dimethylamine in 100 ml of benzene.

15.9 g (0.046 mol) of the crude base are converted into the oxalate using 4.15 g (0.046 mol) of oxalic acid in an ethanolic solution. The pure oxalate is obtained after recrystallisation from ethanol/ethyl acetate; melting point 189°–190° C.

2-Chloro-5,5,10,11-tetrahydro-5-[N-(chloroacetyl)-imino]-dibenzo[b,f]thiepine, which is employed as the starting material, is obtained as follows:

b. 73.5 g (0.3 mol) of 2-chloro-dibenzo[b,f]thiepine are dissolved, with 7.0 g of tris-triphenylphosphine-rhodium chloride in 600 ml of benzene and hydrogenated in an autoclave at 90°–100° C and an initial hydrogen pressure of 50 bars. The absorption of hydrogen is complete after 1 hour. The reaction mixture is cooled and evaporated to dryness in vacuo and the residue is taken up in hot hexane. The resulting suspension is filtered through a short column containing 100 g of silica gel [Merck] and is rinsed well with hot hexane. The resulting eluates are evaporated to dryness and the residue is recrystallised from pentane, 2-chloro-10,11-dihydro-dibenzo[b,f]thiepine being obtained; melting point 65°–66° C.

c. Analogously to Example 4 b), 2-chloro-5,5,10,11-tetrahydro-5-imino-dibenzo[b,f]thiepine is obtained as an oil from 24.6 g (0.1 mol) of 2-chloro-10,11-dihydro-dibenzo [b,f]thiepine and 25.4 g (0.12 mol) of O-mesitylenesulphonylhydroxylamine and is characterised as the hydrochloride; melting point 225°–227° C (decomposition).

d. Analogously to Example 4 c), 2-chloro-5,5,10,11-tetrahydro-5-[N-(chloroacetyl)-imino]-dibenzo[b,f]thiepine is obtained from 26.1 g (0.1 mol) of 2-chloro-5,5,10,11-tetrahydro-5-imino-dibenzo[b,f]thiepine and 13.0 g (0.115 mol) of chloroacetyl chloride and is recrystallised from benzene/petroleum ether; melting point 128°–130° C.

EXAMPLE 12

Analogously to Example 4 a), reaction of 15.1 g (0.050 mol) of 5,5-dihydro-5-[N-(chloroacetyl)-imino]-dibenzo[b,f]thiepine, in each case with the amines shown, in 200 ml of benzene, gives the corresponding compounds of the general formula I.

5,5-Dihydro-5-[N-(N,N-dimethylglycyl)-imino]-dibenzo[b,f]thiepine with 6.8 g (0.151 mol) of dimethylamine;

5,5-dihydro-5-[N-(N-ethylglycyl)-imino]-dibenzo[b,f]thiepine with 6.8 g (0.151 mol) of ethylamine;

5,5-dihydro-5-[N-(N,N-diethylglycyl)-imino]-dibenzo[b,f]thiepine with 8.9 g (0.122 mol) of diethylamine;

5,5-dihydro-5-[N-[2-(1-pyrrolidinyl)-acetyl]-imino]-dibenzo[b,f]thiepine with 8.5 g (0.120 mol) of pyrrolidine;

5,5-dihydro-5-[N-(2-piperidinoacetyl)-imino]-dibenzo[b,f]thiepine with 10.2 g (0.120 mol) of piperidine;

5,5-dihydro-5-[N-[2-(4-methyl-1-piperazinyl)-acetyl]-imino]-dibenzo[b,f]thiepine with 12.0 g (0.120 mol) of 1-methylpiperazine;

5,5-dihydro-5-[N-[2-[4-(2-hydroxyethyl)-1-piperazinyl]-acetyl]-imino]-dibenzo[b,f]thiepine with 15.0 g (0.115 mol) of 1-piperazinoethanol.

EXAMPLE 13

Analogously to Example 4 a), 5,5-dihydro-5-[N-(N-methylglycyl)-imino]-10,11-dimethyl-dibenzo[b,f]thiepine is obtained from 11 g (0.033 mol) of 5,5-dihydro-5-[N-(chloroacetyl)-imino]-10,11-dimethyl-dibenzo[b,f]thiepine [compare Example 5 b) and c)] in 150 ml of benzene using 33 ml (0.165 mol) of a 15% strength methanolic methylamine solution, and 5,5-dihydro-5-[N-(N-methylglycyl)-imino]-10,11-dimethyl-dibenzo[b,f]thiepine is obtained from 10.15 g (0.033 mol) of 10,10-dihydro-10-[N-(chloroacetyl)-imino]-thieno[2,3-b][1] benzothiepine [compare Example 8 b) and c)] in 150 ml of benzene using the same amount of methylamine solution.

EXAMPLE 14

To liberate the base, 21 g of 5,5-dihydro-5-[N-(N-methylglycyl)-imino]-dibenzo[b,f]thiepine oxalate [compare Example 4 a)] are suspended in 250 ml of methylene chloride and the suspension is shaken with 50 ml of concentrated aqueous ammonia solution until all the substance has dissolved. The methylene chloride solution is then washed with twice 50 ml of water, dried over sodium sulphate and evaporated in a waterjet vacuum. Pure, crystalline 5,5-dihydro-5-[N-(N-methylglycyl)-imino]-dibenzo[b,f]thiepine, of melting point 124°–127° C, is obtained as a residue.

To convert the product into the hydrochloride, 19.4 g of the free base are dissolved in 50 ml of isopropanol and 50 ml of methylene chloride and an ethereal hydrogen chloride solution is added, whilst stirring, until the solution gives a weakly acid reaction to congo red. Ether is then added until the solution starts to become turbid and the solution is then stirred for a further 15 minutes, 5,5-dihydro-5-[N-(N-methylglycyl)-imino]-dibenzo[b,f]thiepine hydrochloride crystallising out. Melting point 216° C with decomposition.

What we claim is:

1. An aminoacyl compound of the formula I,

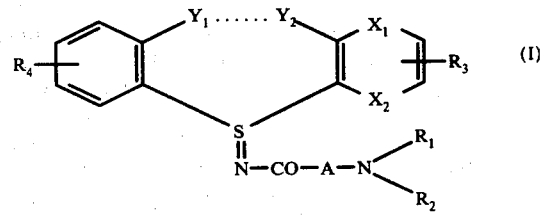

in which $R_1$ and $R_2$ denote hydrogen or lower alkyl groups or, conjointly with the adjacent N atom, denote an alkyleneimino group with 5 to 7 ring members, or a 1-piperazinyl or hexahydro-1H-1,4-diazepin-1-yl group, which is optionally substituted in the 4-position by a lower alkyl group or a lower hydroxyalkyl group, $R_3$ denotes hydrogen, halogen up to atomic number 35 or a lower alkyl or lower alkoxy group, $R_4$ denotes hydrogen, halogen up to atomic number 35 or a lower alkyl, lower alkoxy, trifluoromethyl or nitro group, A denotes a divalent, saturated aliphatic hydrocarbon radical with 1 to 3 carbon atoms and one of the symbols $X_1$ and $X_2$ denotes a direct bond and the other denotes the vinylene group —CH=CH— or the epithio radical —S— and $Y_1$ and $Y_2$ conjointly denote a divalent bridge member $Y_3$ of the following structure:

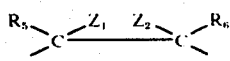

wherein $R_5$ and $R_6$ denote hydrogen or lower alkyl groups and $Z_1$ and $Z_2$ each denote hydrogen or conjointly denote an additional bond, or $R_5$ and $Z_1$ denote hydrogen and, at the same time, $R_6$ and $Z_2$ conjointly denote an oxo radical, or a pharmaceutically acceptable acid addition salt thereof.

2. A compound according to claim 1 having the formula I given in claim 1, in which $X_1$, $X_2$, $Y_1$ and $Y_2$ or $Y_3$ have the meaning defined in claim 1, $R_1$ and $R_2$ independently of one another denote hydrogen or lower alkyl groups with at most 4 carbon atoms or, conjointly with the adjacent nitrogen atom, denote an alkyleneimino group with 5 to 7 ring members or a 1-piperazinyl group, which is optionally substituted in the 4-position by a methyl or 2-hydroxyethyl group, $R_3$ denotes hydrogen, fluorine or chlorine and $R_4$ denotes hydrogen, fluorine or chlorine or a methyl, methoxy, trifluoromethyl or nitro group and A denotes the methylene or ethylene group, or a pharmaceutically acceptable acid addition salt thereof.

3. A compound according to claim 1 having the formula I given in claim 1, in which $X_1$ denotes a direct bond and $X_2$ denotes a vinylene radical or the epithio radical and $Y_1$ and $Y_2$ conjointly as $Y_3$ denote a bridge member of the structure indicated in claim 1, in which $R_5$ and $R_6$ denote hydrogen or methyl groups and $Z_1$ and $Z_2$ denote hydrogen or conjointly denote an additional bond, $R_1$ and $R_2$ independently of one another denote hydrogen or alkyl groups with at most 2 carbon atoms, $R_3$ and $R_4$ independently of one another denote hydrogen, fluorine or chlorine and A denotes a methylene or ethylene group, or a pharmaceutically acceptable acid addition salts thereof.

4. A compound according to claim 1 having the formula I given in claim 1, in which $X_1$ denotes a direct bond and $X_2$ denotes a vinylene radical or the epithio radical and $Y_1$ and $Y_2$ conjointly as $Y_3$ denote a bridge member of the structure indicated in claim 1, in which $R_5$ and $R_6$ denote hydrogen and $Z_1$ and $Z_2$ denote hydrogen or conjointly denote an additional bond, $R_1$ denotes a methyl group and $R_2$ denotes hydrogen or a methyl group, $R_3$ denotes hydrogen and $R_4$ denotes chlorine or hydrogen and A denotes a methylene group, or a pharmaceutically acceptable acid addition salt thereof.

5. A compound according to claim 1 having the formula I given in claim 1, in which $Y_1$ and $Y_2$ conjointly represent a bridge member $Y_3$ of the structure indicated in claim 1, in which $R_5$ and $R_6$ as well as $Z_1$ and $Z_2$ have the meaning indicated in claim 1 and $X_1$, $X_2$, $R_1$, $R_2$, $R_3$, $R_4$ and A also have the meaning indicated in claim 1, or a pharmaceutically acceptable acid addition salt thereof.

6. A compound according to claim 1 having the formula I given in claim 1, in which $Y_1$ and $Y_2$ conjointly represent a bridge member $Y_3$ of the structure indicated in claim 1, in which $R_5$ and $R_6$ as well as $Z_1$ and $Z_2$ have the meaning indicated in claim 1, $X_1$ and $X_2$ have the meaning indicated in claime 1, $R_1$ and $R_2$ independently of one another denote hydrogen or lower alkyl groups with at most 4 carbon atoms or, conjointly with the adjacent nitrogen atom, denote an alkyleneimino group with 5 to 7 ring members or a 1-piperazinyl group, which is optionally substituted in the 4-position by a methyl or 2-hydroxyethyl group, $R_3$ denotes hydrogen, fluorine or chlorine and $R_4$ denotes hydrogen, fluorine or chlorine or a methyl, methoxy, trifluoromethyl or nitro group and A denotes the methylene or ethylene group, or a pharmaceutically acceptable acid addition salt thereof.

7. A compound according to claim 1 having the formula I given in claim 1, in which $X_1$ denotes a direct bond and $X_2$ denotes a vinylene radical or the epithio radical, $Y_1$ and $Y_2$ conjointly represent a bridge member $Y_3$ of the structure indicated in claim 1, in which $R_5$ and $R_6$ denote hydrogen or methyl groups and $Z_1$ and $Z_2$ denote hydrogen or conjointly denote an additional bond, $R_1$ and $R_2$ independently of one another denote hydrogen or alkyl groups with at most 2 carbon atoms, $R_3$ and $R_4$ independently of one another denote hydrogen, fluorine or chlorine and A denotes a methylene or ethylene group, or a pharmaceutically acceptable acid addition salt thereof.

8. A compound according to claim 1 having the formula I given in claim 1, in which $X_1$ denotes a direct bond and $X_2$ denotes a vinylene radical or the epithio radical, $Y_1$ and $Y_2$ conjointly represent a bridge member $Y_3$ of the structure indicated in claim 1, in which $R_5$ and $R_6$ denote hydrogen and $Z_1$ and $Z_2$ denote hydrogen or conjointly denote an additional bond, $R_1$ denotes a methyl group and $R_2$ denotes hydrogen or a methyl group, $R_3$ denotes hydrogen and $R_4$ denotes chlorine or hydrogen and A denotes a methylene group, or a pharmaceutically acceptable acid addition salt thereof.

9. A compound according to claim 1 which is 5,5-dihydro-5-[N-(N-methylglycyl)-imino]-dibenzo[b,f]-thiepine or a pharmaceutically acceptable acid addition salt thereof.

10. A compound according to claim 1 which is 5,5-dihydro-5-[N-(N,N-dimethyl-glycyl)-imino]-10,11-dimethyl-dibenzo[b,f]thiepine or a pharmaceutically acceptable acid addition salt thereof.

11. A therapeutic preparation for the treatment of depression comprising a therapeutically effect amount of a compound according to claim 1 having the formula I given in claim 1, in which $Y_1$ and $Y_2$ conjointly represent a bridge member $Y_3$ of the structure indicated in claim 1, in which $R_5$ and $R_6$ as well as $Z_1$ and $Z_2$ have the meaning indicated in claim 1, and $X_1$, $X_2$, $R_1$, $R_2$, $R_3$, $R_4$ and A also have the meaning indicated in claim 1, or of a pharmaceutically acceptable acid addition salt thereof, together with a pharmaceutical carrier.

12. A therapeutic preparation according to claim 11 wherein a therapeutically effective amount of 5,5-dihydro-5-[N-(N-methylglycyl)-imino]-dibenzo[b,f]thiepine or of a therapeutically effective acid addition salt thereof is present.

13. A method for the treatment of states of depression in a warm-blooded animal comprising administration to said animal of a therapeutically effective amount of a compound according to claim 1 having the formula I given in claim 1, in which $Y_1$ and $Y_2$ conjointly represent a bridge member $Y_3$ of the structure indicated in claim 1, in which $R_5$ and $R_6$ as well as $Z_1$ and $Z_2$ have the meaning indicated in claim 1, and $X_1$, $X_2$, $R_1$, $R_2$, $R_3$, $R_4$ and A also have the meaning indicated in claim 1, or of a pharmaceutically acceptable acid addition salt thereof.

14. A method according to claim 13, wherein 5,5-dihydro-5-[N-(N-methylglycyl)-imino]-dibenzo[b,f]-thiepine or a pharmaceutically effective acid addition salt thereof is used.

* * * * *